US011132424B2

(12) United States Patent
Sanyal et al.

(10) Patent No.: US 11,132,424 B2
(45) Date of Patent: *Sep. 28, 2021

(54) HEALTH MONITORING ECO-SYSTEM WITH OPTIMIZED POWER CONSUMPTION

(71) Applicants: Alodeep Sanyal, San Jose, CA (US); Benjamin Mbouombouo, Saratoga, CA (US); Sankha Bhattacharya, San Jose, CA (US); Nilanjan Banerjee, Elkridge, MD (US); Indranil Sen-Gupta, Fullerton, CA (US)

(72) Inventors: Alodeep Sanyal, San Jose, CA (US); Benjamin Mbouombouo, Saratoga, CA (US); Sankha Bhattacharya, San Jose, CA (US); Nilanjan Banerjee, Elkridge, MD (US); Indranil Sen-Gupta, Fullerton, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 15/653,346

(22) Filed: Jul. 18, 2017

(65) Prior Publication Data

US 2017/0367599 A1    Dec. 28, 2017

Related U.S. Application Data

(63) Continuation of application No. 15/636,073, filed on Jun. 28, 2017.

(Continued)

(51) Int. Cl.
*G06F 19/00*    (2018.01)
*A61B 5/00*    (2006.01)
(Continued)

(52) U.S. Cl.
CPC ........ *G06F 19/3418* (2013.01); *A61B 5/0002* (2013.01); *A61B 5/0022* (2013.01);
(Continued)

(58) Field of Classification Search
CPC ...... G16H 50/20; H04W 4/38; G06F 19/3418
See application file for complete search history.

(56) References Cited

U.S. PATENT DOCUMENTS

2014/0316792 A1* 10/2014 Siddiqui ............. G06F 19/3418
                                                            705/2
2016/0058324 A1*  3/2016 Cao .................... A61B 5/7282
                                                            600/302

(Continued)

FOREIGN PATENT DOCUMENTS

WO    WO-2006102538 A2 *  9/2006  ........... A61B 5/0024

OTHER PUBLICATIONS

Anantha Chandrakasan et al., "Ultralow-Power Electronics for Biomedical Appliations", Apr. 4, 2008, Annual Review of Biomedical Engineering, vol. 10, pp. 247-274 (Year: 2008).*

(Continued)

*Primary Examiner* — Evangeline Barr
(74) *Attorney, Agent, or Firm* — Law Office of Herbert T. Patty (57) ABSTRACT

A power-optimized eco-system for tracking a user's health comprises: one or more wearable remote sensors, each wirelessly communicating only with one wearable central sensor; a portable device readily accessible to the user; and a cloud platform. Each sensor is configured to measure data indicative of one or more physiological parameters. The central sensor is configured to receive and subsequently process data measured by each remote sensor, to process data measured by the central sensor, and to generate corresponding instructions. The portable device comprises: a receiver wirelessly receiving the processed data and instructions from the central sensor; a processor running a mobile application handling the processed data and instructions; and a transmitter. The cloud platform is configured to: receive the processed data from the transmitter; analyze the received (Continued)

processed data; and transmit the results of the analysis to at least one of the portable device and an authorized healthcare entity.

12 Claims, 6 Drawing Sheets

Related U.S. Application Data (60) Provisional application No. 62/355,507, filed on Jun. 28, 2016.

(51) Int. Cl.
| | |
|---|---|
| *H04L 29/08* | (2006.01) |
| *G16H 50/20* | (2018.01) |
| *G16H 40/67* | (2018.01) |
| *G16H 40/63* | (2018.01) |
| *H04W 4/38* | (2018.01) |
| *A61B 5/04* | (2006.01) |
| *H04M 1/725* | (2006.01) |
| *A61B 5/053* | (2006.01) |
| *A61B 5/01* | (2006.01) |
| *A61B 5/024* | (2006.01) |
| *A61B 5/11* | (2006.01) |
| *A61B 5/0404* | (2006.01) |
| *G06N 20/00* | (2019.01) |
| *G06Q 10/06* | (2012.01) |
| *H04L 29/06* | (2006.01) |
| *A61B 5/02* | (2006.01) |
| *A61B 5/0402* | (2006.01) |
| *A61B 5/0488* | (2006.01) |
| *A61B 5/0533* | (2021.01) |
| *A61B 5/0205* | (2006.01) |
| *H04L 29/00* | (2006.01) |

(52) U.S. Cl.
CPC .............. *A61B 5/0024* (2013.01); *A61B 5/02* (2013.01); *A61B 5/04* (2013.01); *A61B 5/0402* (2013.01); *A61B 5/6801* (2013.01); *A61B 5/681* (2013.01); *A61B 5/6803* (2013.01); *A61B 5/74* (2013.01); *A61B 5/742* (2013.01); *A61B 5/746* (2013.01); *G06F 19/321* (2013.01); *G06N 20/00* (2019.01); *G06Q 10/06* (2013.01); *G16H 40/63* (2018.01); *G16H 40/67* (2018.01); *G16H 50/20* (2018.01); *H04L 29/06* (2013.01); *H04L 65/40* (2013.01); *H04L 67/04* (2013.01); *H04L 67/10* (2013.01); *H04L 67/12* (2013.01); *H04L 67/22* (2013.01); *H04L 67/30* (2013.01); *H04W 4/38* (2018.02); *A61B 5/01* (2013.01); *A61B 5/02055* (2013.01); *A61B 5/02416* (2013.01); *A61B 5/0404* (2013.01); *A61B 5/0488* (2013.01); *A61B 5/0533* (2013.01); *A61B 5/1114* (2013.01); *A61B 5/6814* (2013.01); *A61B 5/6816* (2013.01); *A61B 5/6823* (2013.01); *A61B 5/6826* (2013.01); *A61B 5/6828* (2013.01); *A61B 5/6829* (2013.01); *A61B 5/6831* (2013.01); *A61B 5/6838* (2013.01); *A61B 5/6843* (2013.01); *A61B 5/72* (2013.01); *A61B 5/7267* (2013.01); *A61B 5/7275* (2013.01); *A61B 2560/0209* (2013.01); *A61B 2560/0223* (2013.01); *G06F 19/00* (2013.01); *H04L 29/00* (2013.01); *H04L 67/00* (2013.01); *H04L 67/306* (2013.01); *H04M 1/7253* (2013.01); *H04M 1/72541* (2013.01); *Y02D 70/00* (2018.01); *Y02D 70/10* (2018.01); *Y02D 70/12* (2018.01); *Y02D 70/126* (2018.01); *Y02D 70/1262* (2018.01); *Y02D 70/14* (2018.01); *Y02D 70/142* (2018.01); *Y02D 70/144* (2018.01); *Y02D 70/20* (2018.01); *Y02D 70/26* (2018.01)

(56) References Cited

U.S. PATENT DOCUMENTS

2016/0328991 A1* 11/2016 Simpson ................ A61B 5/742
2016/0367202 A1* 12/2016 Carter .................. A61B 5/7289

OTHER PUBLICATIONS

Patel S, Park H, Bonato P, Chan L, Rodgers M. A review of wearable sensors and systems with application in rehabilitation. J Neuroeng Rehabil. 2012;9:21. Published Apr. 20, 2012. doi:10.1186/1743-0003-9-21 (Year: 2012).*

* cited by examiner

HEALTH MONITORING ECO-SYSTEM WITH OPTIMIZED POWER CONSUMPTION

CROSS-REFERENCE

This application claims priority to U.S. application Ser. No. 15/636,073, filed Jun. 28, 2017, which in turn claims priority to Provisional Application No. 62/355,507, filed Jun. 28, 2016, both of which are incorporated herein by reference in their entirety, as if set forth in full in this application for all purposes.

OVERVIEW

A non-invasive multi-sensor eco-system tracks and monitors critical human physiological parameters, including those covered by the term "vital signs," to detect and predict health conditions. The system may be operated in an adaptive mode. The physiological parameters are extracted from a plurality of sensors using novel algorithms. The parameters measured by one embodiment may include blood pressure, heart rate, oxygen saturation (SpO2), respiratory rate, blood glucose level, body temperature and physical activity measured as step count.

The eco-system consists of multiple components wirelessly communicating with each other: (1) wearable sensors, which may include signal processing functionality as well as wireless inter-sensor communication and short-term data storage; (2) a portable computing device hosting a mobile application which enables reception of the processed sensed data, transmission of that data to a cloud platform for analysis, display of push notifications determined by the processed sensed data, reception of analysis results fed back from the cloud platform, and visualization of the processed sensed data and of the cloud analytics data; and (3) the cloud platform itself, allowing long-term data storage as well as analysis of the measurement data to obtain short and long-term health trends and future health predictions. In some embodiments the eco-system also includes a linked healthcare provider, for professional review and action as and when necessary or appropriate.

The eco-system operates to (a) analyze the physiological parameters derived from data provided by two or more sensors, positioned at different locations over the subject's body; (b) compare them against their respective normal, critical and life-threatening bounds as defined by the clinical community; and (c) provide feedback, alerts, push notifications and/or 911 calls depending on the criticality of the results of the comparison. Machine learning algorithms may be employed to carry out various aspects of the analysis, at the cloud platform level.

BACKGROUND

With the increase in the size of the elderly population, as well as the emergence of chronic diseases on a broader population segment, largely influenced by changes in modern lifestyle, coupled with rapid increase in healthcare costs, there has been a significant need to monitor the health status and overall wellbeing of individuals in their daily routine to prevent serious health disorders. Alongside, we observe an increase in thirst for quantification of one's own health on a continuous basis. The adoption of mobile healthcare technology promises to enhance the quality of life for chronic disease patients and the elderly, as well as healthy individuals. Furthermore, it offers the potential to alter the modality of the current healthcare system by enhancing the scope of out-patient care and by reducing the need for hospitalizations and other cost-intensive healthcare needs.

Some solutions have been proposed to address issues in this area, but none of them has provided a closed and comprehensive eco-system as envisaged by the present invention.

There is, therefore, a need for systems and methods that allow for continuous non-invasive health monitoring technology—a disruptive technology, in the sense that it would alter the perspective of healthcare from reactive to proactive. The eco-system would ideally be closed-loop and comprehensive, covering a spectrum of actions, from automatically collecting physiological parameters from each of a plurality of users, getting a full understanding of the parameter profile for each individual user, and recording their long-term health trends and conditions, to providing guidance toward attaining a healthier lifestyle for individual users, groups and the community as a whole.

DETAILED DESCRIPTION

The manner in which the present invention provides its advantages over systems in current use can be more easily understood with reference to FIGS. 1 through 4. It should be noted that throughout this disclosure, the words "user", "patient", and "subject" are used interchangeably.

Figure 1:
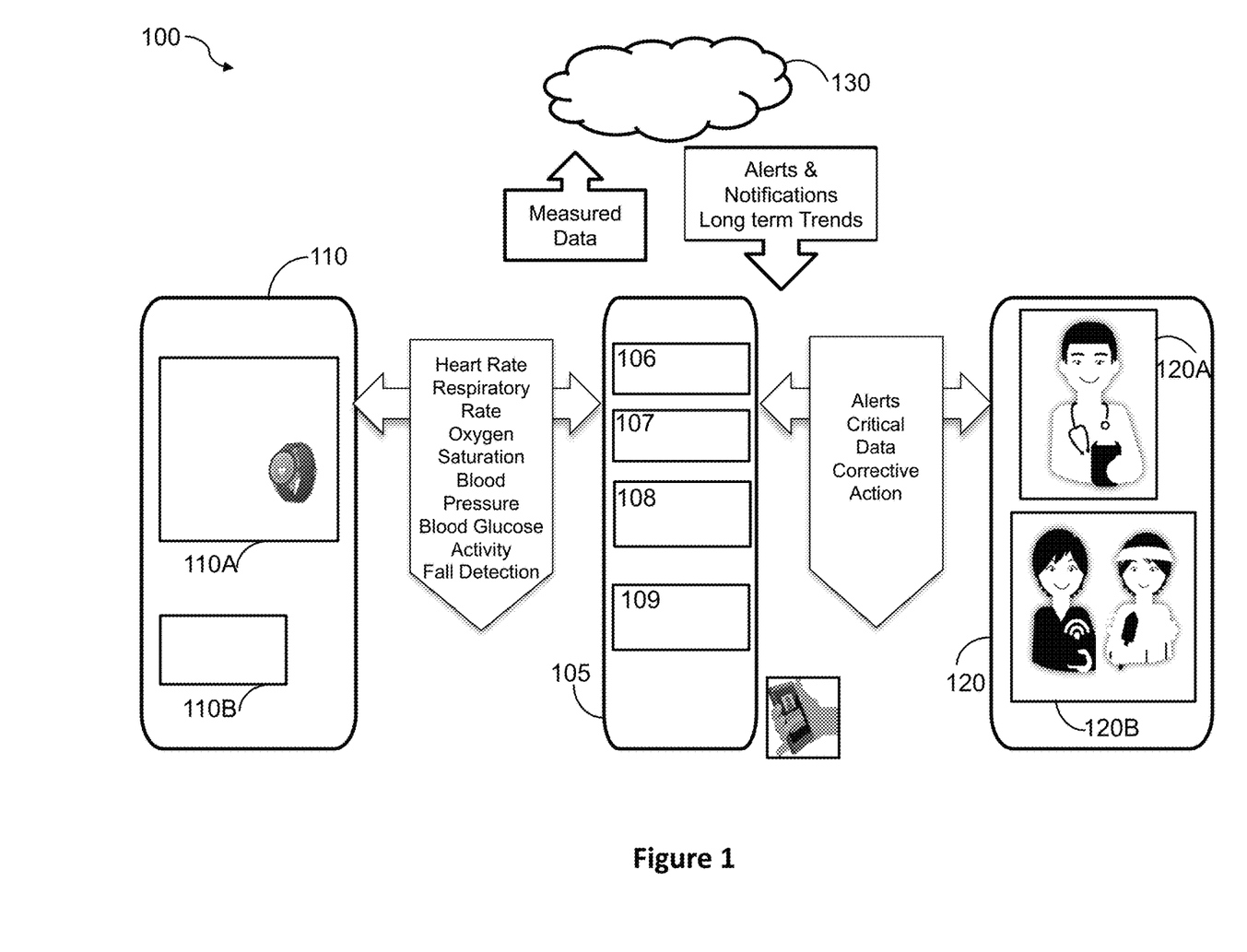
FIG. 1 illustrates a high level view of an eco-system according to one embodiment of the invention.

FIG. 1 is a high level view of an eco-system 100 of the present invention, illustrating relationships between four major elements—sensors 110 (central sensor 110A and just one remote sensor 110B are shown in this example for simplicity, but in other embodiments, there may be additional remote sensors), a cloud platform 130 hosting AI-based analytics, and a mobile or portable device 105. Device 105 has a user interface enabling communication with the sensors, the platform, and with an entity 120, typically comprising a healthcare entity, which may, for example, be a physician, a clinic, or an emergency care unit. Entity 120 may also include a user chosen sub-community of people such as family members. These various elements make up a closed or self-contained, independently functioning eco-system, which in this embodiment includes entity 120. In some embodiments, entity 120 may be considered to lie outside the eco-system, but to be in communication with it. In the embodiment shown in FIG. 1, a single healthcare entity 120A is communicatively coupled to mobile device 105 and directly or indirectly to cloud platform 130. In another embodiment, not shown, there may be two or more different healthcare entities, one in communication with the cloud platform and the other in communication with the mobile device.

FIG. 1 indicates how a system of continuous and adaptive vital data monitoring with clinical accuracy may result in a healthier lifestyle and peace of mind.

Figure 2:
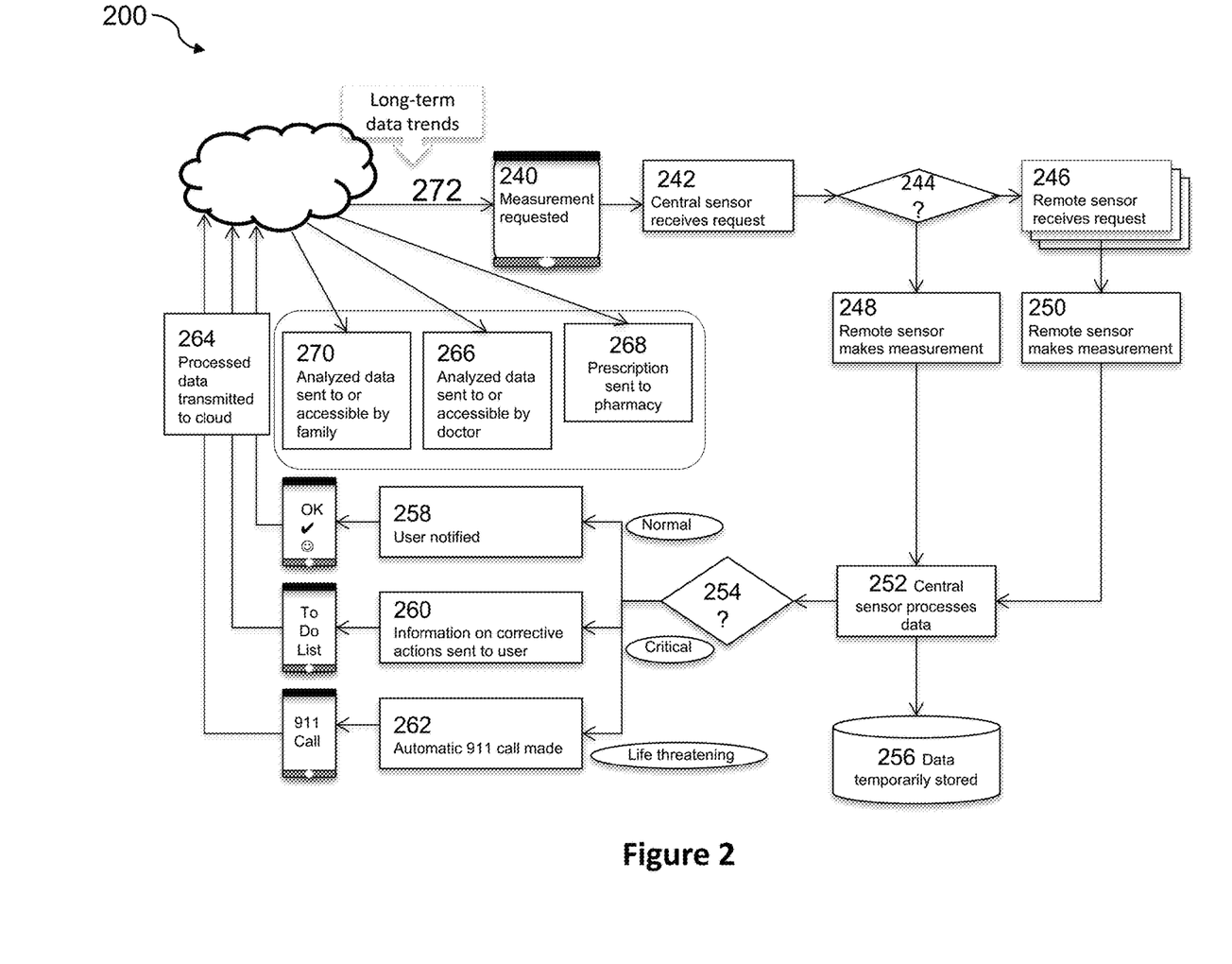
FIG. 2 schematically illustrates the functioning of an eco-system according to one embodiment of the invention.

FIG. 2 illustrates the functioning of elements of an eco-system 200 according to the present invention, showing a finer granularity level than FIG. 1, and illustrating some of the steps performed by components of the closed-loop ecosystem.

One element or category is a plurality of wearable sensors (110 in FIG. 1), including one central sensor and one or more auxiliary or remote sensors worn by a user. Each sensor is configured to monitor one of the user's physiological parameters. Examples of typical parameters of interest are listed in Table 1.

TABLE 1

| | |
|---|---|
| 1. | Heart Rate |
| 2. | Pulse Rate |
| 3. | Heart Rate Variability |
| 4. | Cardiac Index |
| 5. | Blood Pressure |
| 6. | Blood Glucose |
| 7. | Respiratory Rate |
| 8. | Oxygen Saturation (SpO2) |
| 9. | Desaturation Index |
| 10. | Apnea Hypopnea Index |
| 11. | Body Temperature |
| 12. | Electrocardiograph Activity |
| 13. | Electro Dermal Activity |

As shown in FIG. 2, measurements of one or more of these parameters may be initiated at step 240, as and when desired by the user, using an interface of an application on a convenient portable device easily accessed by the subject, such as a smart-phone (105 in FIG. 1). Alternately, the parameters may be automatically measured as programmed in such an application. Components of device 105 include receiver 106, transmitter 107, processor 108, and display screen 109.

The central sensor is typically worn on the wrist; typical locations for other sensors include the forehead, chest, fingertip, earlobe and leg. Examples of measurement technologies used include photoplethysmography (PPG), electrocardiography (ECG), 3-axis accelerometry, temperature measurement using thermistors, and electrodermal activity monitoring. Some of the sensors (often those at the forehead, earlobe and fingertip) may be used primarily or solely to provide calibration signals for other sensors.

Figure 3:
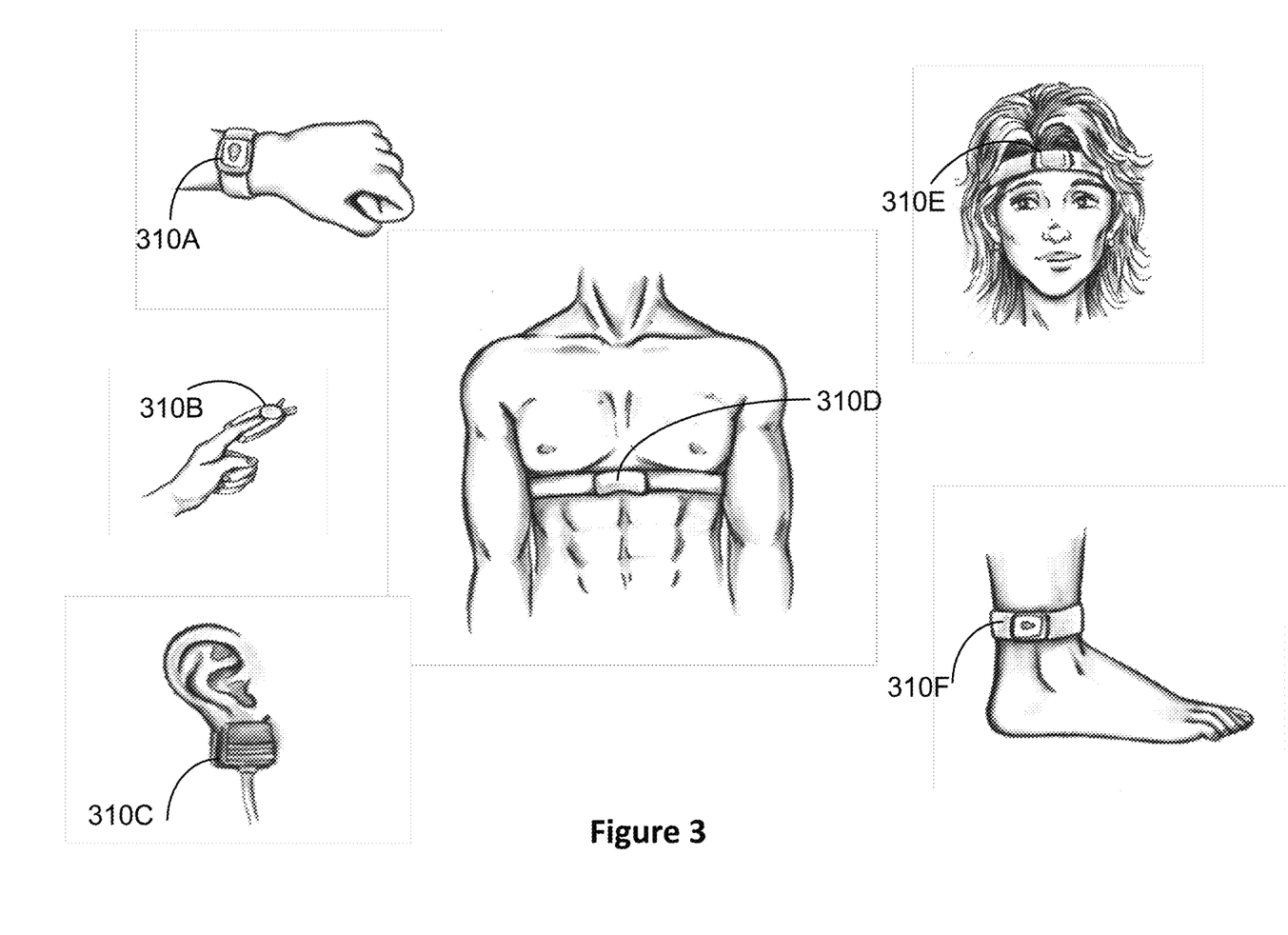
FIG. 3 illustrates examples of sensors that may be worn in various embodiments of the invention.

FIG. 3 shows close up views of examples of sensors at their envisaged body locations. Sensor 310A is a wrist-mounted sensor, typically the central sensor of the system. Sensors 310B, 310C, 310D, 310E, and 310F are examples of sensors designed to be worn on "remote" locations such as a finger tip, earlobe, around the chest, head, or ankle respectively.

Figure 4:
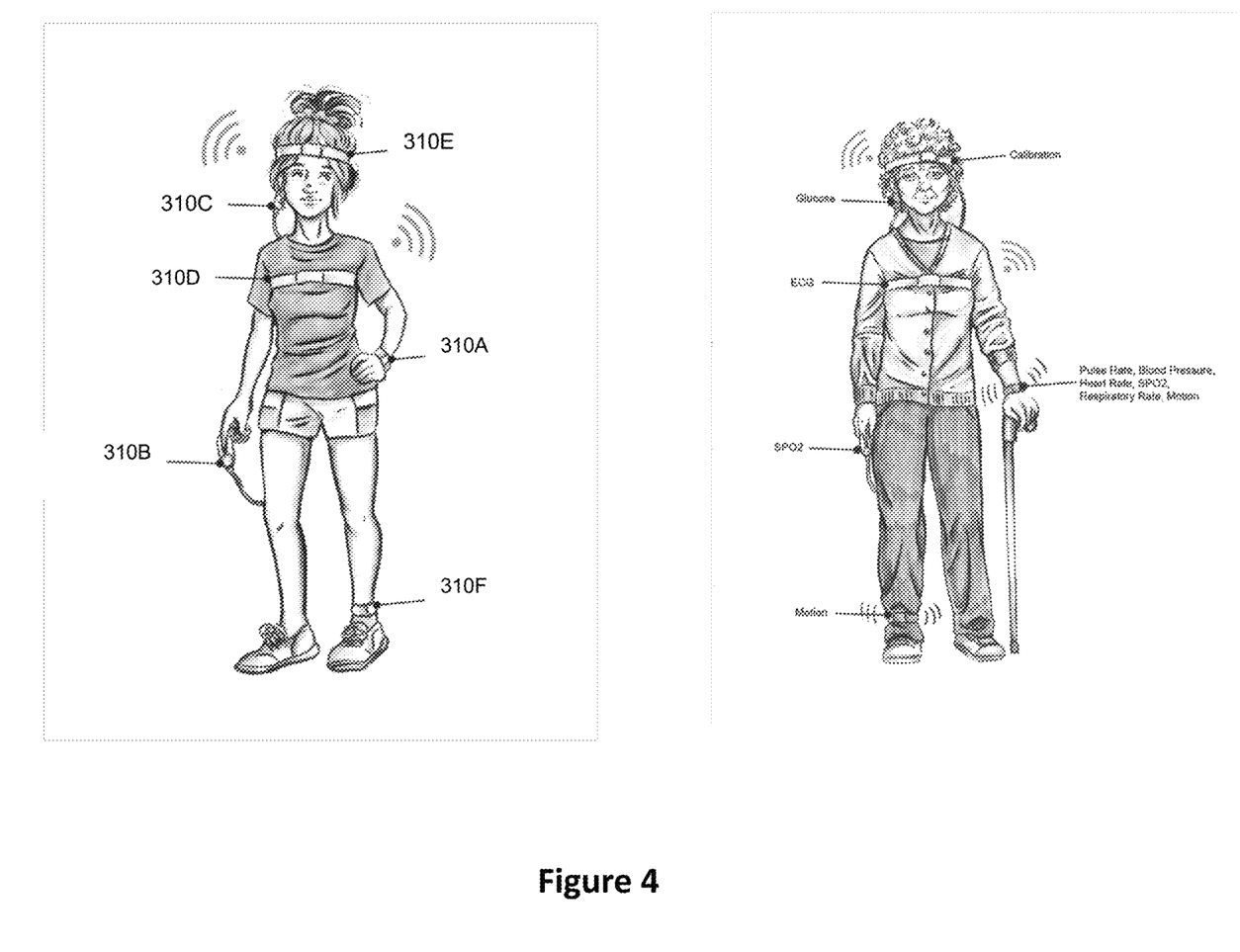
FIG. 4 illustrates two examples of subjects wearing sensors according to embodiments of the invention.

FIG. 4 illustrates how such sensors may be worn by two subjects at different stages of life. The wireless communication of data between the central sensor and each remote sensor may be carried out using Bluetooth or other well-known and established wireless technologies. The placement of sensors 310A-F is shown on the youthful figure on the left, while the corresponding physiological parameters that may be measured using those sensors are shown on the elderly figure on the right. In different embodiments of the invention, a subset of the sensors shown may be used, with as few as one remote sensor present in addition to one central sensor.

In some embodiments, a single sensor may provide data indicative of more than one physiological parameter of interest. One example of this is a photoplethysmographic (PPG) sensor, which essentially monitors blood volume, but from which data indicative of SpO2, glucose, heart rate, blood pressure, and respiratory rate may be derived. Sensors may be operated to monitor the wearer's vital parameters continuously and automatically over long periods of time.

Returning to FIG. 2, once the measurement instructions are issued at step 240 and received by the central sensor at step 242, central sensor selects at step 244 which sensor or sensors are required to perform the desired measurement or measurements. If necessary, the request is transmitted to a remote sensor at step 246. Each designated sensor (central or remote) performs the measurements of the corresponding parameter or parameters at steps 248 and/or 250 respectively. Any measurements performed by remote sensors (such as a leg sensor for example) are wirelessly sent to the central sensor (typically the sensor worn on the subject's wrist), with that central sensor taking responsibility for aggregating the other sensors' data as and when necessary, processing them at step 252, as will be described in greater detail below, and transmitting the results to the user interface on the mobile device, typically a smart-phone.

Calibration plays an important role in attaining clinical-grade accuracy for all measurements of physiological parameters. Two methods may be used to address the calibration issue:

1. Static calibration: Measurement of a parameter using the proposed apparatus is compared against the gold standard (clinical setting measurement) and repeated for a large and diverse set of individuals. The measurement error computed is used to determine the calibration coefficients for the given parameter. The calibration coefficients thus obtained are applied to every apparatus manufactured. The calibration coefficients do not change for the lifetime of operation for a given apparatus.

2. Dynamic AI-based calibration: The calibration coefficients of a given parameter are dynamically computed on cloud platform based on data from a large population bucketed according to age, sex, race, skin color, skin thickness etc. As new data points get added into a specific population bucket, the calibration coefficients get recomputed and adjusted into the settings of a given apparatus used by an individual. The calibration coefficients in this method get constantly adjusted and improved over the lifetime of the apparatus or device performing the parameter measurement of interest.

The second method, dynamic calibration, clearly provides some significant advantages in terms of specificity for the individual, and long term reliability. In the present invention, both static calibration—the current standard practice—and dynamic calibration may be used, to provide a desirable combination of accuracy, convenience, specificity and reliability.

Figure 5:
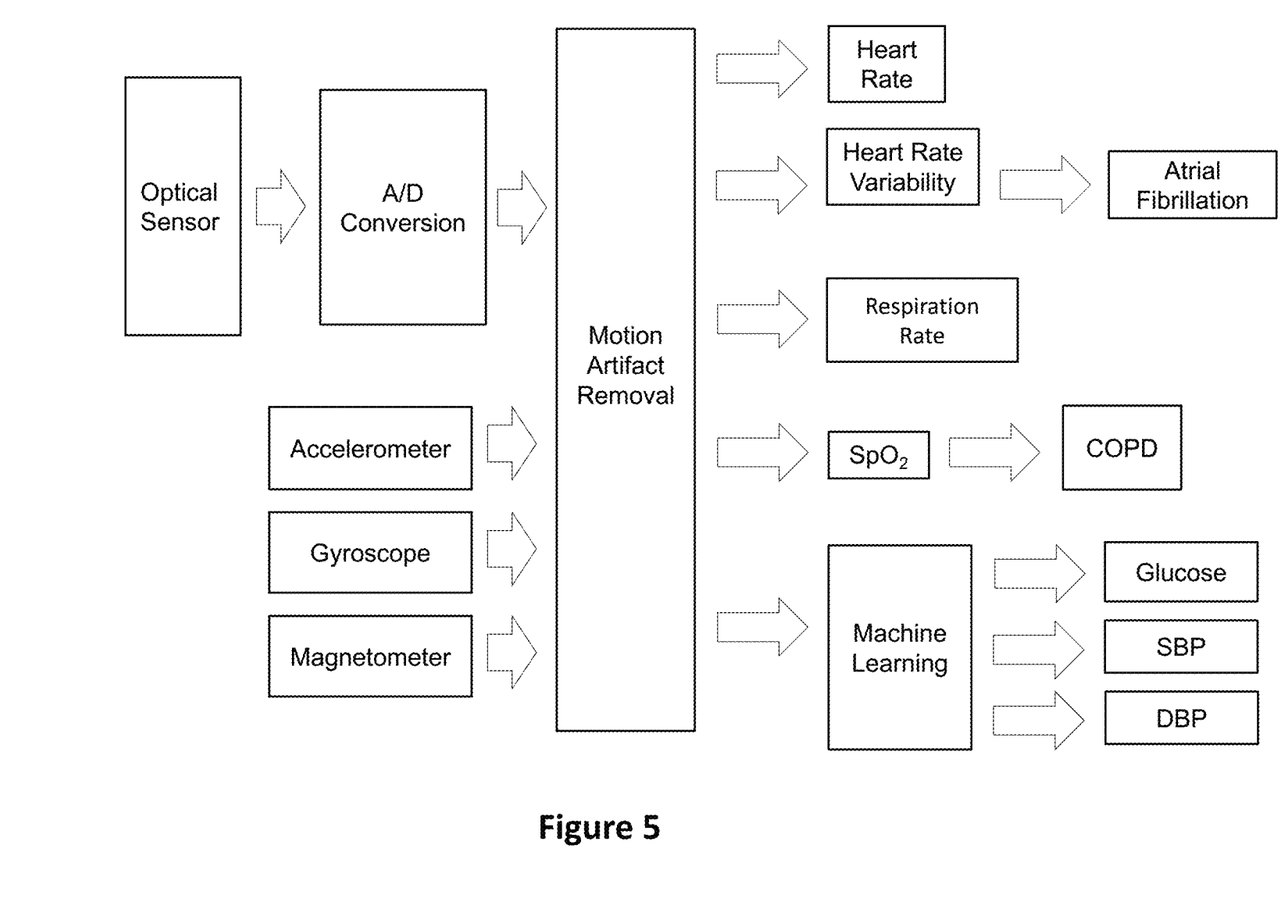
FIG. 5 illustrates the computational flow of data through some embodiments of the invention.

Returning to FIG. 2, at step 252, as noted above, the central sensor processes (filters, calibrates, scales, etc) the raw data received to generate physiological parameter data with accuracies sufficient to render the parameter data clinically meaningful. Specially developed hardware-embedded algorithms may be used to achieve real-time signal processing. FIG. 5 schematically illustrates the computational flow of data gathered by various sensors, and processed by hardware-embedded algorithms according to some embodiments of the present invention, to yield data of clinical significance. The central sensor then compares those processed data values to values defining ranges of interest (normal, critical and life-threatening) for each corresponding parameter, at step 254. The measured and processed data may be stored for the short term in the memory of the central sensor, at step 256. Depending on the results of the comparisons, the central sensor may wirelessly send push notifications to the smart-phone (or similar portable device). These notifications may be normal text, or in some embodiments, simple symbols or easily appreciated codes. For example, at step 258, a blue code, or a predetermined symbol such as a smiley face may be sent to indicate to the subject that a parameter is within normal bounds, an orange code may be sent at step 260 to indicate that the parameter is outside normal bounds but within critical bounds, or a red code may be sent at step 262 to indicate life-threatening bounds have been exceeded. In some embodiments, audible alerts may be issued as well as or instead of visible ones. In the case of a life-threatening situation (red alert), the smart-phone may automatically initiate a 911 call.

In some embodiments, not shown in this figure, alerts may be sent to medical professionals such as the user's personal physician, or to health centers or emergency services. In less serious cases, alerts may be sent just to the user, accompanied by recommendations on relevant corrective actions.

One advantage of the present invention is that the data processing and transmission burdens of the entire group of sensors is carried by just the central sensor, easing the power consumption and size, weight, complexity and cost demands on the remote sensors.

Figure 6:
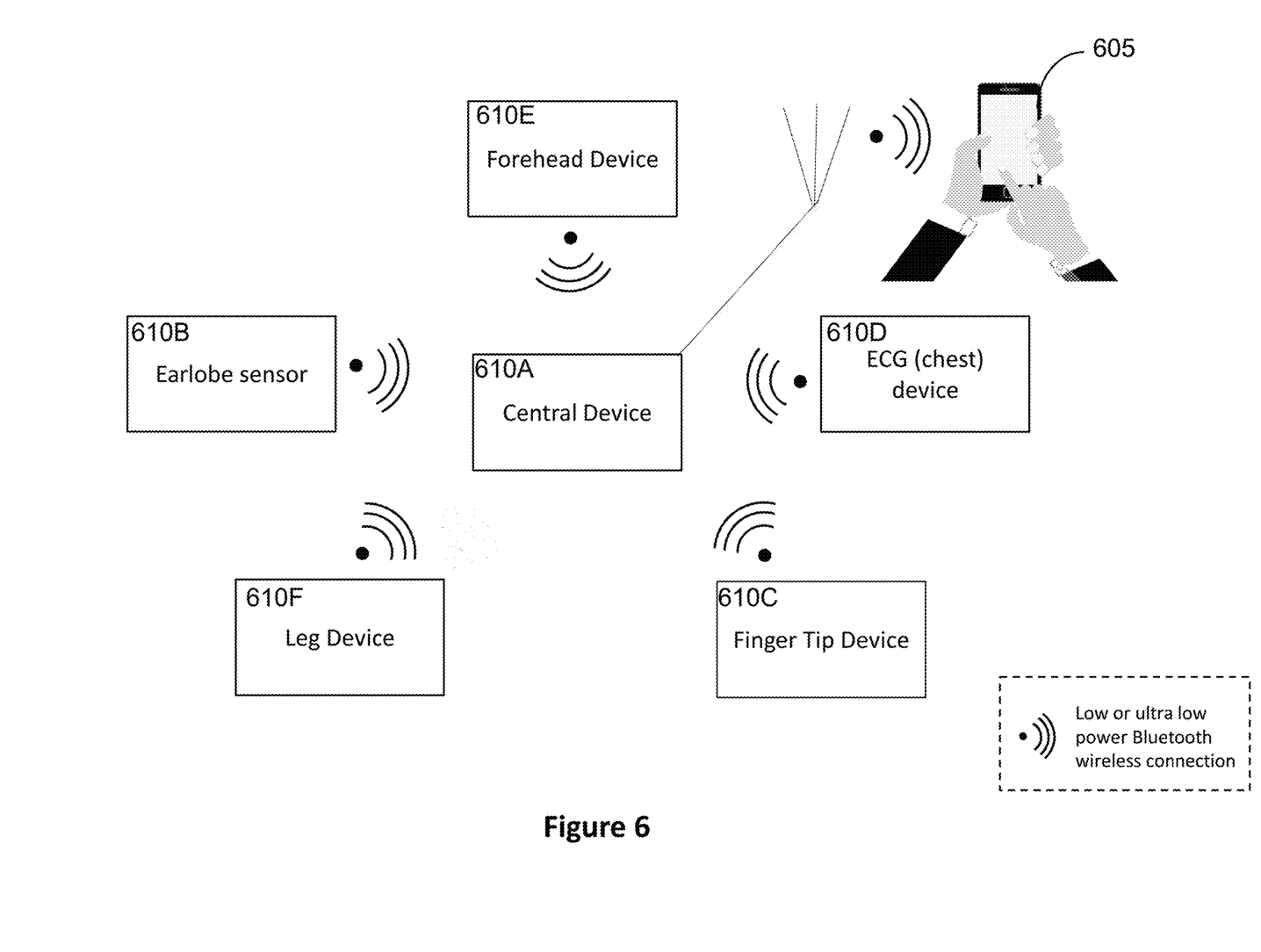
FIG. 6 illustrates low power connectivity between hardware elements in some embodiments of the invention.

FIG. 6 schematically illustrates one embodiment in which ultra short range (0.5 m to 1 m), ultra low power (1 to 10 microwatt range) Bluetooth wireless connections are provided between central sensor 610A and five remote sensors 610 B-F, and a slightly longer range (1.5 m) low power (100 microwatt to 300 microwatt) Bluetooth connection is provided between central sensor 610A and mobile (in this case hand-held) device 605. In other embodiments, other similar low and ultra low power protocols may be used. Reduced power consumption results in longer battery lifetime and reduced device heating, so better reliability.

At step 264, the smart-phone (or other portable device) then uses the standard internet service (e.g. 4G, LTE, WiFi etc) to securely send the processed data to the cloud for long-term storage and analytics as will be described further below. It should be noted that the use of just one device—the smart-phone or similar device—to handle the transmission of processed data to the cloud significantly simplifies system design and power consumption relative to the situations common today, where each sensor of a plurality worn by a subject independently processes and transmits data to distant receivers. In the present invention, the remote sensors only have to transmit data over very short distances to reach the central sensor, which then sends processed data to the smart-phone, which in turn transmits them to the cloud, and receives other data (such as trend data discussed below) back. The display screen on the smart-phone (or PDA or tablet) allows the subject to receive push alerts and easily visualized displays of the results of the cloud-based analytics.

The cloud provides long term storage of the data received from the smart-phone, and carries out analysis using conventional and/or machine learning algorithms. The machine learning algorithms may be especially useful when applied to the stored physiological parameter data to provide information on long-term trends, and to yield personalized measurement data that are wirelessly sent back to the smart-phone.

The machine learning algorithms may also use the received and stored data regarding one or a combination of the parameters measured to determine health conditions or clinical insights (examples of which are listed below in Table 2) relevant to the individual subject. Predictions regarding future health may be made.

TABLE 2

| | |
|---|---|
| 1. | COPD (Chronic Obstructive Pulmonary Disease) |
| 2. | Congestive Heart Failure (CHF) |
| 3. | Cardiovascular diseases |
| 4. | Cardiac Arrhythmia |
| a. | Atrial Fibrillation (from ECG) |
| b. | Ventricular Tachycardia (leading to Ventricular Fibrillation) |
| 5. | Stress Level |
| 6. | Sleep Apnea and Hypopnea |
| 7. | Personalized Meal Recommendation |
| 8. | Bodyweight Regulation |
| 9. | Pre-diabetic/Diabetic Stages |
| 10. | Hypothermia and Fever |
| 11. | Involuntary Fall and Seizure |
| 12. | Cholesterol Level |
| 13. | Hypertension |
| 14. | Dehydration |

Specialized, in some cases unique, algorithms may be used to provide the determinations, insights, and predictions. Table 3 lists examples of some of the types of specialized algorithms envisaged. In some embodiments, the "normal" parameter ranges relative to which the wearer's parameters are compared may be customized according to sex, race, weight, height, and/or other characteristics. Data may be analyzed over time and presented in a way that a user can monitor the progress of his/her health status for a given set of parameters.

TABLE 3

SpO2 extraction algorithm
Heart rate extraction algorithm
Heart rate variability extraction algorithm
Blood pressure extraction algorithm
Respiratory rate extraction algorithm
Blood glucose level extraction algorithm
Desaturation index computation algorithm
Cardiac index computation algorithm
Apnea Hypopnea index computation algorithm As indicated by step 266 in FIG. 2, the processed parameter data, trend data and clinical insights data (or some subset of such data) may be sent from the cloud directly or indirectly to a physician at a medical facility authorized by the subject to receive them. Upon reviewing the data, the physician may provide advice, guidance, education, and/or prescriptions to the patient (user). Prescriptions from the patient's doctor may then be wirelessly and securely sent via the cloud to a pharmacy pre-selected by the subject as part of his or her personal profile, the profile having been previously created by the subject at a secure website, accessed via the smart-phone or other computing device. Users can also update their profiles directly from a smart-phone.

As indicated by step 268, some or all of the processed data may be sent from the cloud directly or indirectly to family members of the user, pre-authorized to receive such data.

The user's physician, other selected health professionals, family members, and others, make up a specific user-defined community, authorized to access data provided by the cloud platform relating to that user.

Analytics performed in the cloud can also provide long-term trends for vital parameters and clinical insights to a subject. These long-term trends consist of vital parameters measured over the course of many months or event years that is displayed in a receiver like a smart-phone, a tablet, or a computer.

As indicated by step 272, the analytics carried out at the cloud may result in suggestions, transmitted back to the user via the smart-phone, for adjusting the sequence and/or frequency of measurements of particular parameters. The system may even request additional measurements of the same or other parameters if the previous measurements deviate from the predefined user specific range. For instance, an elevated temperature can trigger the automatic measurement of blood pressure, ECG, oxygen saturation, etc.

In this way and others discussed above or readily envisaged in the light of this disclosure, the eco-system can be adaptive, responding to current measurement data in the light of past data from the same subject and/or other comparable subjects, whether to appropriately instigate future measurements, inform the subject of trends, or to add to the physician's knowledge base enabling more effective guidance and treatment.

Additional Examples and Details (1) Hardware Embedded Algorithms for Real-Time Vital Signal Processing Unique mathematical algorithms will process the raw PPG signal generated by the LED/Photo-Diode/AFE
  SpO2 extraction algorithm
  Heart rate extraction algorithm
  Heart rate variability extraction algorithm
  Blood pressure extraction algorithm
  Respiratory rate extraction algorithm
  Blood glucose level extraction algorithm
  Desaturation index computation algorithm
  Cardiac index computation algorithm
  Apnea Hypopnea index computation algorithm (2) Application for Smart Phone, Tablets, Laptop as User Interface, Data and Alerts Display Alert System
  The alert system has different severity level visualized by different colors
  Color green means a specific vital parameter is within the normal range
  Color yellow means that a specific vital parameter has exceeded the normal bounds but within a critical range
  Color orange means that a specific vital parameter has exceeded the critical bounds but still below the life-threatening range
  Color red means a specific vital parameter has exceeded the life-threatening bounds and an emergency call (such as, the 911 call in US) is automatically initiated.

A red alert is automatically issued for any life-threatening situation. In this case, a central monitoring facility first tries to establish a contact with the user, and upon no response, an emergency call (such as the 911 in US) is issued with a message about the location of the patient and the specific body parameter(s) in question. This will ensure the correct paramedic team with the correct equipment arrive at the scene on time and well prepared to save the life of the patient. The red alert is handled in an automatic way to address cases where a patient is unconscious and cannot make an emergency call (such as, 911) or even express him/herself. The user can also issue a red alert if a vital parameter is in a life-threatening range and the system has not yet issued a 911 call.

User Interface
  User can enter personal information called user profile
  User can request instant measurement of specific vital parameter
  User can request to view trend data (3) Analytics: Software and Machine Learning Algorithms for Data Pattern and Trend Analysis The cloud-based analytics platform allows for the secured collection and long-term hosting of all personalized vital parameter data. It allows for
  The creation of new multi-parameter machine learning algorithms to automatically derive the current state of various physiological vital parameters [002] and related health conditions for an individual user
  Automatic derivation of deviations from the baseline for each of these parameters
  Automatic derivation of a long-term trend for each of the vital parameters
  Automated alerts that go out from the cloud back to the users, family and medical support staff
  Derivation of gradual changes in baselines only observed over long periods of time
  Prediction of future health-critical events for an individual user based on her own health data points and a population of health data (from a population bucket of individuals similar to the user in context) annotated with respective health-critical events
  Special software algorithms developed to use the incoming vital sign data or combination of multiple vital signs data to provide long-term trends and insights for various health conditions.
  Personalized subject vital sign monitoring: Other embedded algorithms will study a subject body to adjust the sequence or frequency of measurements of vital parameters. This specific data is personalized to a subject's health status.
  Derivation of secondary health insights (such as body weight, body hydration level) from the primary vital parameters.
  Creation of a personalized scoring and recommendation of food items based on their impact on various vital parameters.
  Derivation of functioning status and health of major organs (such as liver, pancreas, and kidney) from the primary vital parameters measured. For liver health, enzyme levels in the blood critical for proper functioning of this organ can be detected, the parameters to track are Aspartate Aminotransferase (AST), Alanine Aminotransferase (ALT), alkaline phosphatase, bilirubin, albumin and total protein. For kidney health, the parameters to track are Blood Urea Nitrogen (BUN), creatinine, estimated glomerular filtration rate, and for the pancreas health, the important parameters are Amylase, Lipase and Calcium.
  Derivation of various vitamin levels in blood from the primary vital parameters measured.
  Derivation of blood parameters possibly indicating an elevated risk of presence of some form of cancer cells on the body from primary vital parameters measured. Some specific blood parameters include alkaline phosphatase, Lactate dehydrogenase (LDH), carcinoembryonic antigen (CEA), and prostate-specific antigen (PSA).

Derivation of other blood parameters, such as blood albumin level, amount and changes in Flavin, which can be useful in determining changes in different enzymatic levels, blood pH levels and anemic conditions. Changes in lipid levels will be used to show the trend of arterial blockages.

(4) Personalized Health Monitoring System Adaptive to Individual Physique and Lifestyle (PHMSYSTEM):

An individual is many ways different physically compared to every other person and also the lifestyle choices of that person over a period of time and the changes thereof reflect on all vital health parameters measured instantaneously and/or over a time period. The apparatus described in this patent when used by an individual, "learns" about the user's unique physique and lifestyle choices over a period of time and adjusts its pattern of measurement of vital parameters. These changes in measurement patterns over time affect the overall operating efficiency of the apparatus (such as battery power consumption and heating). These changes help the apparatus become more adaptive to an individual with the continuous use of it and "blends" into the unique patterns of life of that individual. The enhancement of the quality of life of any given individual is a key outcome of the individual adaptive nature of this system. The apparatus is capable of being set into different operating modes such as an adaptive mode (as described above), a traditional mode where every measurement occurs at certain frequency, and a continuous mode where the apparatus keeps taking measurements on a continuous basis.

(5) Individualized Food and Nutrition with the Help of Adaptive Personal Health Monitoring Food and nutrition are keys to status of health of an individual. An individually adaptive personalized health monitoring system is at the center of personalization and individualization of nutrition. The proposed apparatus starts to "learn" about the effects of various food items on the measured vital health parameters of an individual as soon as the individual starts to use it. Over a period of time the apparatus acquires adequate "knowledge" of impact of various food items on the individual's overall wellbeing and estimates trend of health based on the eating habit and recommendations on how to improve it.

(6) Continuous and Adaptive Health Monitoring as a Service (CAHMaaS)

While most healthy people do not monitor their vital data at all between yearly medical checkups and various medical appointments, those suffering from non-life threatening chronic disease requiring continuous monitoring are not as consistent in doing so as recommended by medical professionals. CAHMaaS® offer the possibility to continuously monitor one's vital data through the use of a wearable device that measures vital data and saves them in a secured cloud server. The collected data are then analyzed through advanced analytics to offer the users real time clinical insights, adapted to the specific conditions of each user through the use of machine learning algorithms. The use of CAHMaaS® requires monthly and/or yearly subscription as well as the ownership of a device providing the required measurements. CAHMaaS® is in the context of Internet-of-life or an embodiment of Internet-of-life. The service based health monitoring system is at the heart of individual adaptiveness of the device to every user's unique physique and lifestyle over a period of time. The individualized adaptive system would help create a tailored ecosystem for individual consumer, the ecosystem might comprise of many things like personal wellness program, customized nutrition etc, the "tailored ecosystem" as one key application as a direct result of CAHMaas.

(7) Sensors

Central Device at Wrist (PPG)
    (1) LED (optical signal transmitter)
    (2) Photodiode (optical signal receiver)
    (3) Analog Module (signal amplification and A/D conversion)
    (4) MicroProcessing Unit (finite state machine, integer/FP units, data path)
    (5) Memory
    (6) Host Controller Interface (HCI)
    (7) Low-power Bluetooth Interface
    (8) Three-axis Accelerometer (3D positioning)
    (9) Thermistor/Thermopile
    (10) Battery and charger unit Remote Device at Chest (ECG)
    The chest apparatus collects ECG signals that will be wirelessly sent to the central apparatus for further processing and storage.

Remote Device at Earlobe
    The earlobe apparatus is used to collect data that gets wirelessly sent to the central apparatus to calibrate other vital signs for better accuracy.

Remote Device at Finger Tip
    The finger tip apparatus is used to collect data that gets wirelessly sent to the central apparatus to calibrate other vital signs for better accuracy.

Remote Device at Leg
    The three-axis accelerometer is strapped at the bottom leg part to monitor the leg movements to process a 3-dimensional position of the user that is wirelessly communicated to the central apparatus Remote Device at Forehead
    The forehead apparatus is used to collect data that is wirelessly sent to the central apparatus to calibrate other vital signs for better accuracy.

The above-described embodiments should be considered as examples of the present invention, rather than as limiting the scope of the invention. Various modifications of the above-described embodiments of the present invention will become apparent to those skilled in the art from the foregoing description and accompanying drawings.

What is claimed is:

1. An adaptive power-optimized eco-system for tracking health of a user, the eco-system comprising:
an electrodermal activity sensor configured to be worn by the user;
a blood glucose sensor configured to be worn by the user;
each of said electrodermal sensor and said blood glucose sensor configured to communicate with a wearable central sensor, said central sensor configured to receive and subsequently process first electrodermal activity data measured by said electrodermal activity sensor and to generate corresponding instructions responsive to said electrodermal activity data, said corresponding instructions comprising an automatically triggered order, transmitted from said central sensor to said glucose sensor, to collect glucose data.

2. The power-optimized eco-system of claim 1, wherein each of said electrodermal activity sensor and said glucose sensor communicates with the central sensor using a wireless link operating at a power level below 10 microwatt.

3. The power-optimized eco-system of claim 1, wherein the central sensor communicates with the portable device using a wireless link operating at a power level below 300 microwatt.

4. The power-optimized eco-system of claim 1, wherein each of said electrodermal activity sensor and said glucose sensor communicates with the central sensor using low power Bluetooth technology or ultra low power Bluetooth technology.

5. The power-optimized eco-system of claim 1, wherein a portable device communicates with the cloud platform using one of 4G, LTE, and Wi-Fi technologies.

6. The power-optimized eco-system of claim 1, wherein the central sensor is worn on a wrist of the user and wherein each of said electrodermal activity sensor and said glucose sensor is worn on a different part of the user's body, the different part being one of the forehead, the chest, a fingertip, an earlobe and a leg of the user.

7. The power-optimized eco-system of claim 1, wherein measurement technologies used by the central sensor include at least one of photoplethysmography (PPG), electrocardiography (ECG), 3-axis accelerometry, and temperature measurement using thermistors.

8. The power-optimized eco-system of claim 1, said central sensor used to provide calibration signals for another sensor worn by the user.

9. The power-optimized eco-system of claim 1, wherein said central sensor provides data indicative of more than one physiological parameter of interest.

10. The power-optimized eco-system of claim 1, wherein the central sensor achieves real-time signal processing of data measured by said glucose sensor using specially developed hardware-embedded algorithms.

11. The power-optimized eco-system of claim 10, wherein the central sensor compares the processed data to values defining ranges of interest (normal, critical and life-threatening) for each corresponding parameter, and generates corresponding instructions, before transmitting the processed data and instructions to a portable device.

12. A method for operating an adaptive power-optimized eco-system for tracking health of a user, comprising the steps of:
- a wearable central sensor receiving data measured by each of: an electrodermal activity sensor worn by the user and a glucose sensor worn by the user, each of said electrodermal activity sensor and said glucose sensor being configured to measure data indicative of one or more physiological parameters of the user,
- the central sensor processing the data received from the electrodermal activity sensor; and
- responsive to electrodermal activity data from said electrodermal activity sensor, automatically triggering an order, transmitted from said central sensor to said glucose sensor, to collect glucose data,
- the central sensor wirelessly transmitting processed data to a receiver in a portable device communicatively coupled to the central sensor and readily accessible to the user;
- a processor in the portable device running a mobile application handling the processed data and instructions;
- a transmitter in the portable device transmitting the processed data to a cloud platform; and
- the cloud platform automatically analyzing the received processed data, generating results; and transmitting the results of the analysis to at least one of the portable device and an authorized healthcare entity; wherein the results include instructions to the portable device regarding future data measurements.

* * * * *